(12) United States Patent
Oliver et al.

(10) Patent No.: US 7,728,214 B2
(45) Date of Patent: Jun. 1, 2010

(54) USING MUSIC TO INFLUENCE A PERSON'S EXERCISE PERFORMANCE

(75) Inventors: Nuria Maria Oliver, Seattle, WA (US); Fernando Flores-Mangas, Mexico City (MX)

(73) Assignee: Microsoft Corporation, Redmond, WA (US)

( * ) Notice: Subject to any disclaimer, the term of this patent is extended or adjusted under 35 U.S.C. 154(b) by 152 days.

(21) Appl. No.: 11/407,493

(22) Filed: Apr. 20, 2006

(65) Prior Publication Data
US 2007/0113726 A1    May 24, 2007

Related U.S. Application Data

(60) Provisional application No. 60/739,181, filed on Nov. 23, 2005.

(51) Int. Cl.
G10H 7/00 (2006.01)
(52) U.S. Cl. ....................................................... 84/612
(58) Field of Classification Search .................. 84/612, 84/636
See application file for complete search history.

(56) References Cited

U.S. PATENT DOCUMENTS

| | | | | |
|---|---|---|---|---|
| 6,572,511 | B1 * | 6/2003 | Volpe | 482/4 |
| 6,623,427 | B2 * | 9/2003 | Mandigo | 600/300 |
| 7,566,290 | B2 * | 7/2009 | Lee et al. | 482/8 |
| 2006/0107822 | A1 * | 5/2006 | Bowen | 84/612 |
| 2006/0111621 | A1 * | 5/2006 | Coppi et al. | 600/300 |
| 2006/0243120 | A1 * | 11/2006 | Takai et al. | 84/612 |
| 2006/0276919 | A1 * | 12/2006 | Shirai et al. | 700/94 |
| 2007/0074619 | A1 * | 4/2007 | Vergo | 84/612 |

OTHER PUBLICATIONS

"About FMOD," fmod.org, © 2001-2005 Firelight Technologies, Pty, Ltd., <http://www.fmod.org/fmodmain.html> [retrieved Mar. 20, 2006].

"About jogTunes," jogTunes.com, © 2005-2006 PDS Company, <http://jogtunes.com> 2006 [retrieved Mar. 22, 2006].

Anshel, M.H., and D.Q. Marisi, "Effect of Music and Rhythm on Physical Performance," *Research Quarterly* 49(2):109-112, 1979.

Becker, N., et al., "Mellow and Frenetic Antecedent Music During Athletic Performance of Children, Adults, and Seniors," *Perceptual and Motor Skills* 79(2):1043-1046, 1994.

Beckett, A., "The Effects of Music on Exercise As Determined by Physiological Recovery Heart Rate and Distance," *Journal of Music Therapy* 27(3):126-136, 1990.

"Interval Running iTunes Playlist," Lifehacker.com, Feb. 14, 2006, <http://www.lifehacker.com/software/running/interval-running-itunes-playlist-154491.php> [retrieved Mar. 22, 2006].

(Continued)

*Primary Examiner*—Jeffrey Donels
(74) *Attorney, Agent, or Firm*—Lee & Hayes, PLLC

(57) ABSTRACT

Aspects of the invention use music to influence a person's performance in a physical workout. A computing device receives and analyzes data indicating current physiology and movement of the user in order to provide a music piece that will influence the user to speed up, slow down, or maintain current pace so to achieve a desired exercise performance level. Information specific to the user may be considered in providing the music piece.

17 Claims, 13 Drawing Sheets

OTHER PUBLICATIONS

"iPod: Which iPod Are You?" apple.com, © 2005 Apple Computer, Inc., <http:/www.apple.com/ipod> [retrieved Mar. 20, 2006].

Kravitz, L., "The Effects of Music on Exercise," *IDEA Today* *12*(9):56-61, 1994.

Lee, W., "The Effect of Music on Walking Performance of Older Adults," master's thesis [abstract], Ball State University, 2001.

Melanson, E.L., et al., "Commercially Available Pedometers: Considerations for Accurate Step Counting," *Preventive Medicine* *39*(2):361-368, 2004.

Pitas, I., and A.N. Venetsanopoulos, *Nonlinear Digital Filters: Principles and Applications*, Kluwer Academic Publishers, Boston, Massachusetts, 1990.

Potteiger, J.A., et al., "Influence of Music on Ratings of Perceived Exertion During 20 Minutes of Moderate Intensity Exercise," *Perceptual and Motor Skills* *91*(3):848-854, 2000.

Pujol, T.J., and M.E. Langenfeld, "Influence of Music on Wingate Anaerobic Test Performance," *Perceptual and Motor Skills* *88*(1):292-296, 1999.

"Recommended Fitness Products," polarusa.com, © 2003-2006 Polar <http://www.polarusa.com/consumer/fitness/products.asp> [retrieved Mar. 22, 2006].

Staum, M.J., "Music and Rhythmic Stimuli in the Rehabilitation of Gait Disorders," *Journal of Music Therapy* XX(2):69-87, 1983.

"Suunto Foot POD," Suunto.com, © Sep./Nov. 2004 Suunto Oy, <http://www.suunto.com> [retrieved Jul. 21, 2006].

"Suunto n6HR," Suunto.com, Jul. 1, 2005, <http://www.suunto.com> [retrieved Jul. 21, 2006].

"Suunto t6," Suunto.com, Jan. 7, 2005, <http://www.suunto.com> [retrieved Jul. 21, 2006].

\* cited by examiner

USING MUSIC TO INFLUENCE A PERSON'S EXERCISE PERFORMANCE

CROSS-REFERENCE TO RELATED APPLICATION

This application claims the benefit of U.S. Provisional Application No. 60/739,181, filed Nov. 23, 2005, titled MPTRAIN: MUSIC AND PHYSIOLOGY-BASED PERSONAL TRAINER, which is specifically incorporated by reference herein.

BACKGROUND

Conventionally, an individual often needs to seek the input of a human personal trainer to achieve the individual's exercising goals. The use of a human personal trainer can be expensive and inconvenient. For example, besides paying the human personal trainer, the individual needs to take the human personal trainer along during an exercising routine. Therefore, it is desirable to provide a means allowing a person to achieve his or her exercising goals during an exercising routine without the aid of a human personal trainer.

In addition, music has been part of the exercise routines for many people. Research has identified positive effects of music on exercise performance. For example, different studies agree that music positively influences users' exercise endurance, performance perception, and perceived exertion levels. The reasons proposed to explain such positive effects include that music provides a pacing advantage and a form of distraction from the exercise, that music boosts the moods of users and raises the confidence and self-esteem of the users, and that music motivates users to exercise more. It is therefore desirable to take advantage of the positive effects of music in exercise performance to enable users to more easily achieve their exercise goals.

It is not surprising, therefore, that music has increasingly become part of the exercise routines of more and more people. In particular, in recent years, MP3 players and heart-rate monitors are becoming increasingly pervasive when people exercise, especially when they are walking, running, or jogging outdoors. For example, it has been common in the community of runners to prepare a "running music playlist" to help runners in their training schedules. A runner may even develop a script that creates a running music playlist in which music pieces stop and start at time intervals to indicate when to switch from running to walking without the runner having to check a watch.

However, none of the existing systems directly exploits the effects of music on human physiology during physical activities in an adaptive and real-time manner. The existing systems and prototypes developed so far usually operate in a one-way fashion. That is, they deliver a pre-selected set of music in a specific order. In some cases, they might independently monitor the user's heart rate, but they do not include feedback about the user's state of performance to affect the music update. Therefore, it is desirable to provide a means that monitors a user's physiology and movements and selects music for the user accordingly.

While specific disadvantages of existing practices have been illustrated and described in this Background Section, those skilled in the art and others will recognize that the subject matter claimed herein is not limited to any specific implementation for solving any or all of the described disadvantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Aspects of the invention provide a system (hereafter "MPTrain") that utilizes the positive influences of music in exercise performance to help a user more easily achieve the user's exercising objectives.

One aspect of the invention implements MPTrain as a mobile and personal system that a user can wear while exercising, such as walking, jogging, or running. Such an exemplary MPTrain may include both a hardware component and a software component. The hardware component may include a computing device that a user can carry or wear while exercising. Such a computing device can be a small device such as a mobile phone, a personal digital assistant ("PDA"), a watch, etc. The hardware component may further include a number of physiological and environmental sensors that can be connected to the computing device through a communication network such as a wireless network.

The software component in the exemplary MPTrain may allow a user to enter a desired workout in terms of desired heart-rate stress over time. The software component may assist the user in achieving the desired exercising goals by (1) constantly monitoring the user's physiology (e.g., heart rate in number of beats per minute) and movement (e.g., pace in number of steps per minute), and (2) selecting and playing music with specific features that will guide the user towards achieving the desired exercising goals. The software component may use algorithms that identify and correlate features (e.g., energy, beat or tempo, and volume) of a music piece, the user's current exercise level (e.g., running speed, pace or gait), and the user's current physiological response (e.g., heart rate).

Aspects of the invention thus are able to automatically choose and play the proper music or adjust features of music to influence the user's exercise behavior in order to keep the user on track with the user's desired exercising goals. For example, the music provided can influence the user to speed up, slow down, or maintain the pace in the user's exercise activities to match the desired heart rate for the user at a given time.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The following detailed description provides exemplary implementations of aspects of the invention. Although specific system configurations and flow diagrams are illustrated, it should be understood that the examples provided are not exhaustive and do not limit the invention to the precise form disclosed. Persons of ordinary skill in the art will recognize that the process steps and structures described herein may be interchangeable with other steps and structures, or combinations of steps or structures, and still achieve the benefits and advantages inherent in aspects of the invention.

The following description first provides an overview of an exemplary MPTrain system architecture through which aspects of the invention may be implemented. Section II then describes exemplary algorithms for extracting needed information such as current heart rate and movement speed of a user from raw sensor data. Section III outlines exemplary features used to characterize a music piece. Section IV describes an exemplary algorithm for updating music for a user during the user's exercise routine. Section V provides a description of an exemplary user interface of an exemplary MPTrain system.

I. Overall MPTrain Architecture

Embodiments of the invention implement the MPTrain as a mobile system including both hardware and software that a user can wear while exercising (e.g., walking, jogging, or running). Such an MPTrain system includes a number of physiological and environmental sensors that are connected, for example, wirelessly, to a computing device that a user carries along. The computing device can be a mobile phone, a PDA, etc. Such an MPTrain system may allow a user to enter the user's desired exercise pattern, for example, through a user interface on the computing device.

Figure 1:
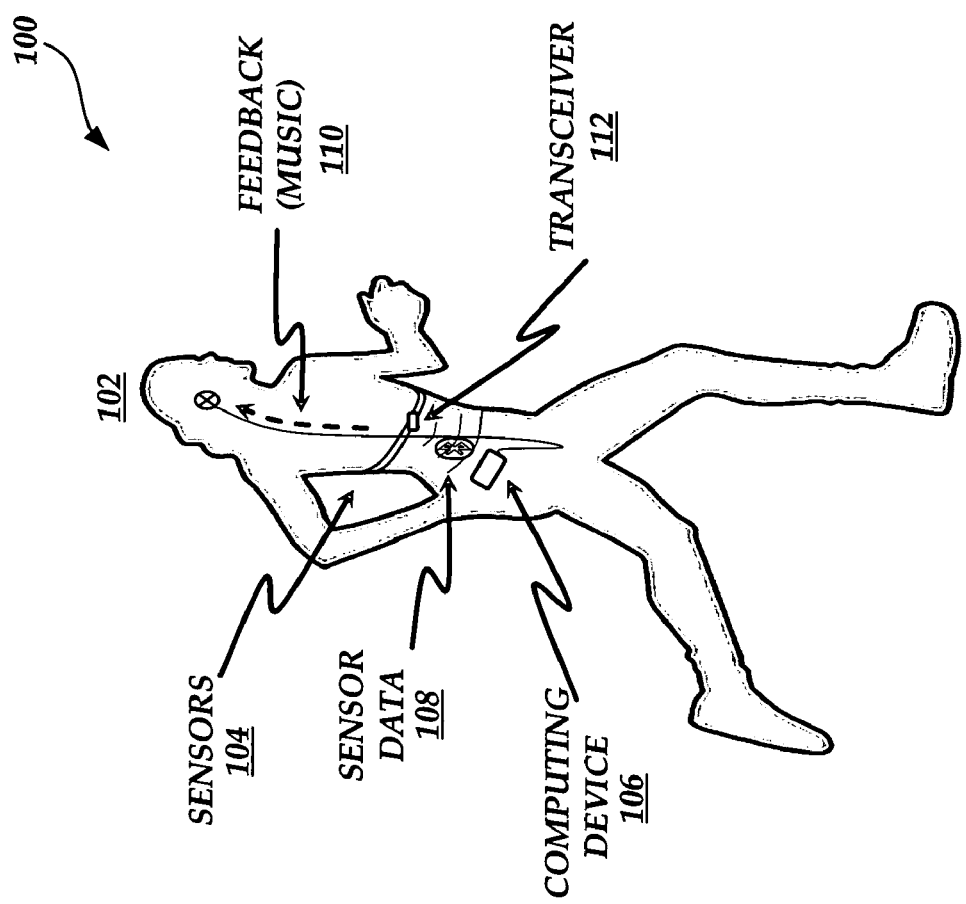
FIG. 1 is a pictorial diagram illustrating an exemplary usage scenario of an exemplary MPTrain system.

FIG. 1 illustrates a typical usage scenario 100 of an exemplary MPTrain system. As shown, a user 102 is running while wearing Bluetooth-enabled sensors 104 such as a heart-rate monitor and an accelerometer, and a Bluetooth-enabled computing device 106 such as a mobile phone. As known by these of ordinary skill in the art, Bluetooth is a computing and telecommunications industry standard that describes how mobile phones, computers, and PDAs can easily interconnect with each other and with home and business phones and computers using a short range (and low power) wireless connection. Embodiments of the invention may also use other communication means for data exchange.

In the usage scenario 100, the computing device 106 functions both as a personal computer for data processing and/or display and a processing personal music player. As the user 102 runs, the user 102 listens to music that has been provided to the computing device 106. Meanwhile, the sensors 104 send sensor data 108 (via Bluetooth, for example) in real-time to the computing device 106. A transceiver 112 may be provided for transmitting and receiving data such as the sensor data 108. The computing device 106 collects and stores the sensor data 108. Optionally, the computing device 106 may also present the sensor data 108 to the user 102, for example, after processing the sensor data 108. The computing device 106 then uses the sensor data 108 to update the music 110 to be played next so to help the user 102 achieve the desired exercise pattern.

In embodiments of the invention, the sensors 104 may measure one or more physiological parameters of the user 102, such as heart rate, blood oxygen level, respiration rate, body temperature, cholesterol level, blood glucose level, galvanic skin response, ECG, and blood pressure. The sensors 104 may also gather information to determine the position and behavior of the user 102, such as how fast the user 102 is exercising in terms of steps per minute. The sensor data 108 collected from the sensors 104 can be forwarded to the computing device 106 for storage, analysis, and/or display.

Figure 2:
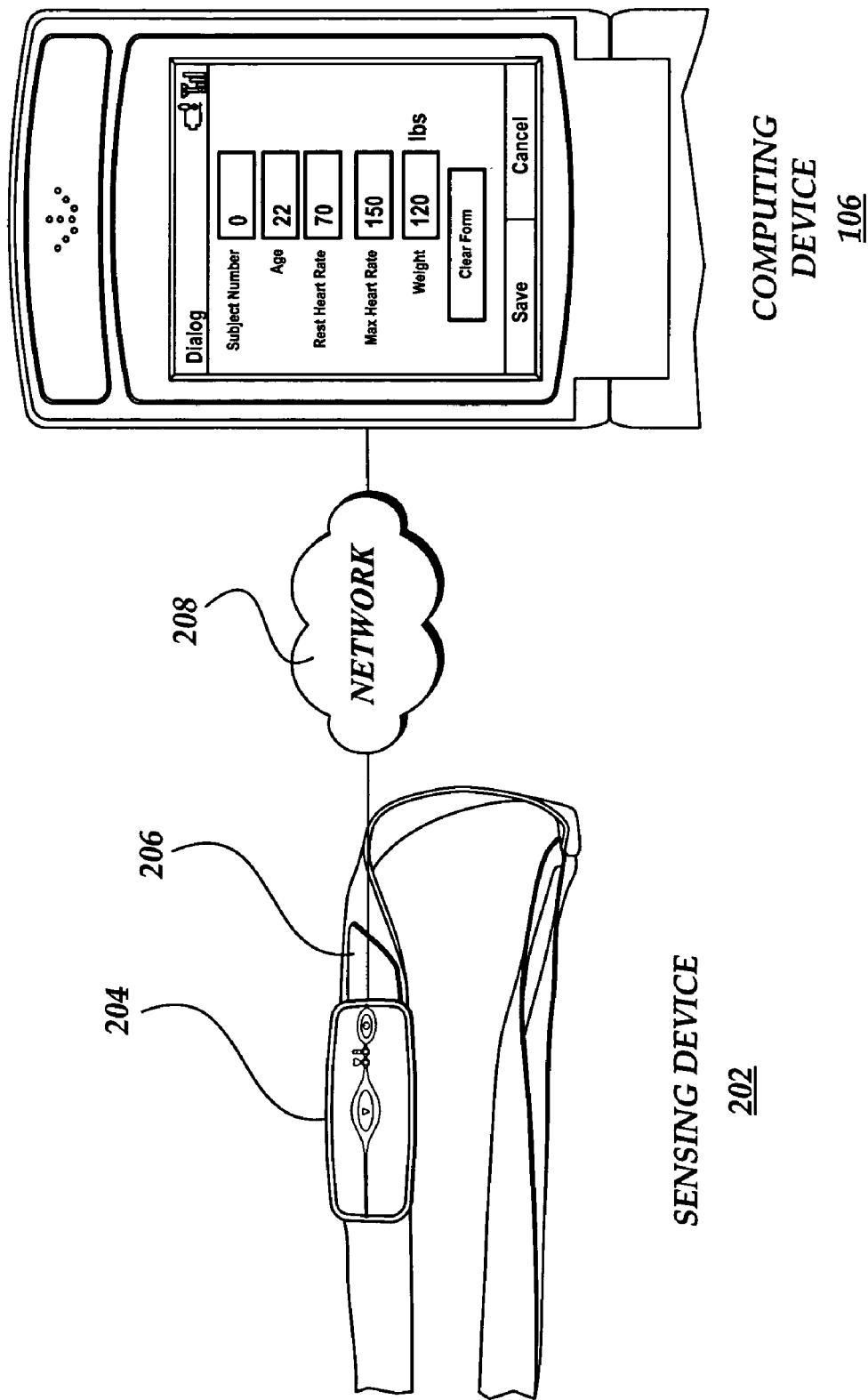
FIG. 2 is a pictorial diagram illustrating exemplary hardware used in an exemplary MPTrain system.

FIG. 2 illustrates exemplary hardware 200 used in an exemplary embodiment of the invention. As shown, the exemplary hardware 200 includes a sensing device 202 and the computing device 106. The sensing device 202 incorporates the sensors 104. The sensing device 202 may further incorporate a battery for power, communication means for interfacing with a network 208, and even a microprocessor for conducting any necessary computation work. In exemplary embodiments of the invention, the network 208 is a wireless communication network.

In an exemplary embodiment, the sensing device 202 is a lightweight (e.g., 60 g with battery) and low-power (e.g., 60 hours of operation with continuous wireless transmission) wearable device that monitors the heart rate and the movement speed of the user 102. The exemplary sensing device 202 may include a heart-rate monitor 204, a chest band 206 with ECG sensors for measuring the heart rate of the user 102, as well as an accelerometer for measuring the movement of the user 102. For example, in an exemplary implementation, the sensing device 202 may include a single-channel ECG with two electrodes (e.g., 300 samples per second), a two-axis accelerometer (e.g., 75 samples per second), an event button, and a secure digital card for local storage. Such an exemplary sensing device 202 may have an efficient power management that allows for continuous monitoring for up to one week, for example. The sensing device 202 may also include a Bluetooth class 1 (e.g., up to 100 m range) transmitter. The transmitter sends the resultant sensor data 108 to the computing device 106, using, for example, a Serial Port Profile, client connection. After collecting the sensor data 108, the sensing device 202 sends them to the computing device 106 via a network 208.

In embodiments of the invention, the computing device 106 may be in various forms, such as a mobile phone, a PDA, etc. The computing device 106 may be connected to peripheral devices, such as auxiliary displays, printers, and the like. The computing device 106 may include a battery for power, non-volatile storage for the storage of data and/or software applications, a processor for executing computer-executable instructions, a graphic display, and communication means for interfacing with the network 208. FIG. 2 illustrates an exemplary computing device 106 that happens to be a mobile phone graphically displaying the received sensor data 108. For example, as shown, the mobile phone can be an Audiovox SMT5600 GSM mobile phone running Microsoft's Windows® Mobile 2003 operating system. This phone has built-in support for Bluetooth, 32 MB of RAM, 64 MB of ROM, a 200 MHz ARM processor, and about five days of stand-by battery life.

In embodiments of the invention, the sensing device 202 and/or the computing device 106 may include some form of computer-readable media. Computer-readable media can be any available media that can be accessed by the sensing device 202 and/or the computing device 106. By way of example, and not limitation, computer-readable media may comprise computer storage media and communication media. Computer storage media includes volatile and non-volatile, removable and non-removable media, implemented in any method of technology for storage of information, such as computer-readable instructions, data structures, program modules, or other data. Computer storage media includes, but is not limited to, RAM, ROM, EEPROM, flash memory, or other memory technology; CD-ROM, digital versatile discs (DVDs), or other optical storage; magnetic cassette, magnetic tape, magnetic disc storage, or other magnetic storage devices; or any other medium which can be used to store the desired information and which can be accessed by the sensing device 202 and/or the computing device 106. Communication media typically embody computer-readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media, such as acoustic, RF, infrared, and other wireless media. Combinations of any of the above should also be included within the scope of computer-readable media.

In one embodiment, a complete MPTrain system containing the exemplary hardware 200 shown in FIG. 2 can run in real-time, uninterruptedly, for about 6 hours before needing to recharge the batteries.

Figure 3:
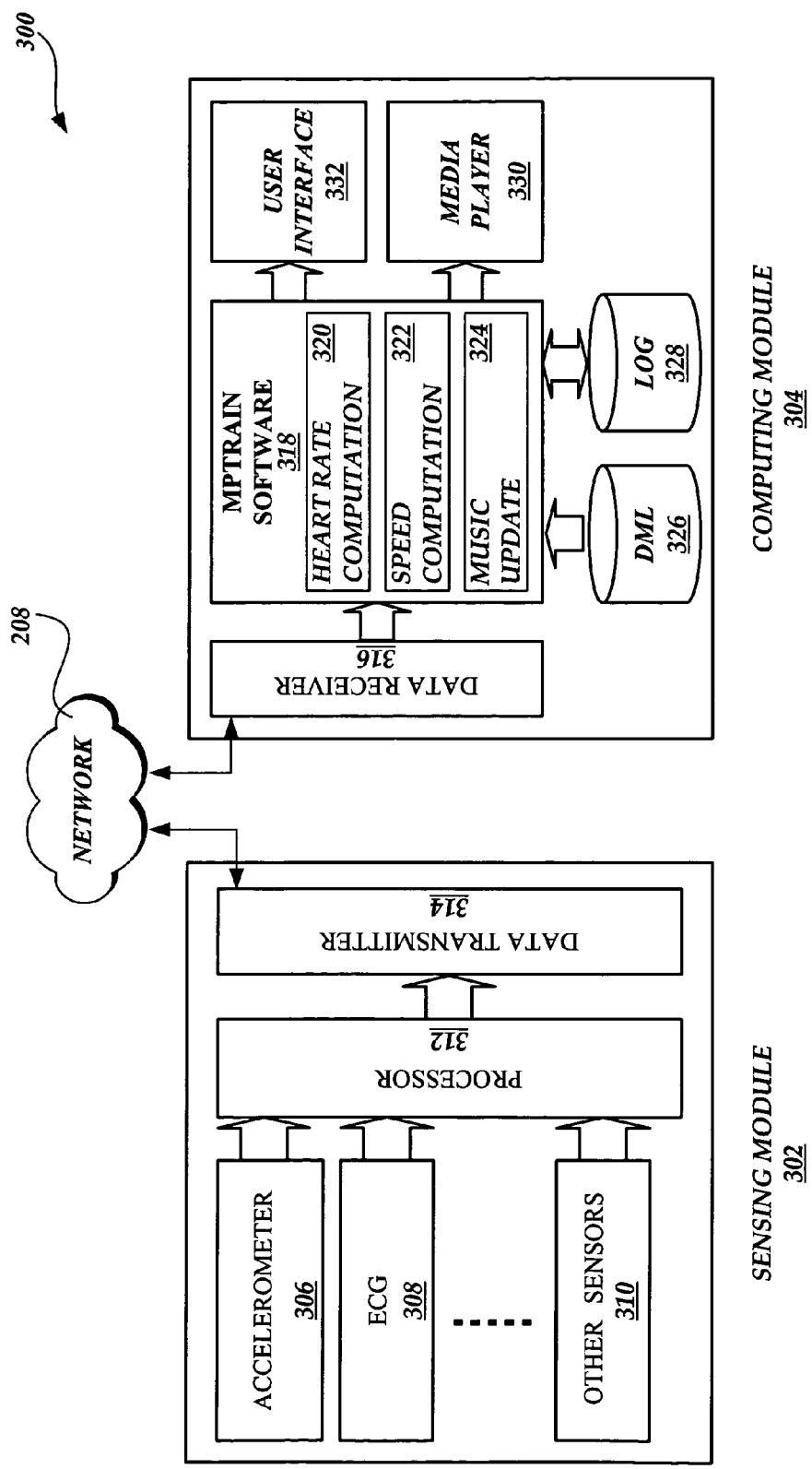
FIG. 3 is a block diagram illustrating an exemplary MPTrain system architecture.

FIG. 3 illustrates an exemplary MPTrain architecture 300 underneath the exemplary hardware 200 illustrated in FIG. 2. The MPTrain architecture 300 includes a sensing module 302 that communicates with a computing module 304 through the network 208. The sensing device 202 shown in FIG. 2 may incorporate the sensing module 302 while the computing device 106 may incorporate the computing module 304.

In embodiments of the invention, the sensing module 304 includes a set of physiological and environmental sensors 104 such as an accelerometer 306, ECG 308, and other sensors 310. The sensing module 304 may further include a processor 312 to receive the sensor data 108, to process them, and to pass them to a data transmitter 314 (e.g., a Bluetooth transmitter). The data transmitter 314 then sends the sensor data 108, via the network 208, to the computing module 304 incorporated in the computing device 106.

FIG. 3 depicts an exemplary computing module 304 and the components within that are relevant to exemplary embodiments of the invention. As shown, corresponding to the data transmitter 314 in the sensing module 302, the computing module 304 includes a data receiver 316 that receives the sensor data 108 from the network 208 and makes them available to MPTrain software 318 in the computing module 304.

In embodiments of the invention, the MPTrain software 318 may receive, analyze, store, and/or display the sensor data 108. In some embodiments of the invention, the received sensor data 108 is raw sensor signals. That is, data analysis and computation needs to be performed on the sensor data 108 in order to extract needed information such as current heart rate and movement speed of the user 102. In one embodiment of the invention, the MPTrain software 318 performs a heart rate computation function 320 using the received sensor data 108 to assess the current heart rate of the user 102. The MPTrain software 318 may also perform a speed computation function 322 to assess the current movement speed of the user 102. FIGS. 5A-5B and 7A-7B illustrate exemplary implementations of the heart rate computation function 320 and the speed computation function 322, and will be described in detail below in Section II.

In alternative embodiments of the invention, the heart rate computation function 320 and the speed computation function 322 may be performed on a device other than the computing device 106. Such a device may be the sensing device 202, for example, where the processor 312 (FIG. 3) may perform the computation and the data transmitter 314 may send the computation results to the computing module 304. The data receiver 312 in the computing module 304 then forwards the computation results to the MPTrain software 318. Alternatively, a third-party device may receive the raw sensor data 108 from the sensing module 302, perform the computation, and then send the computation results to the computing module 304.

Figure 9:
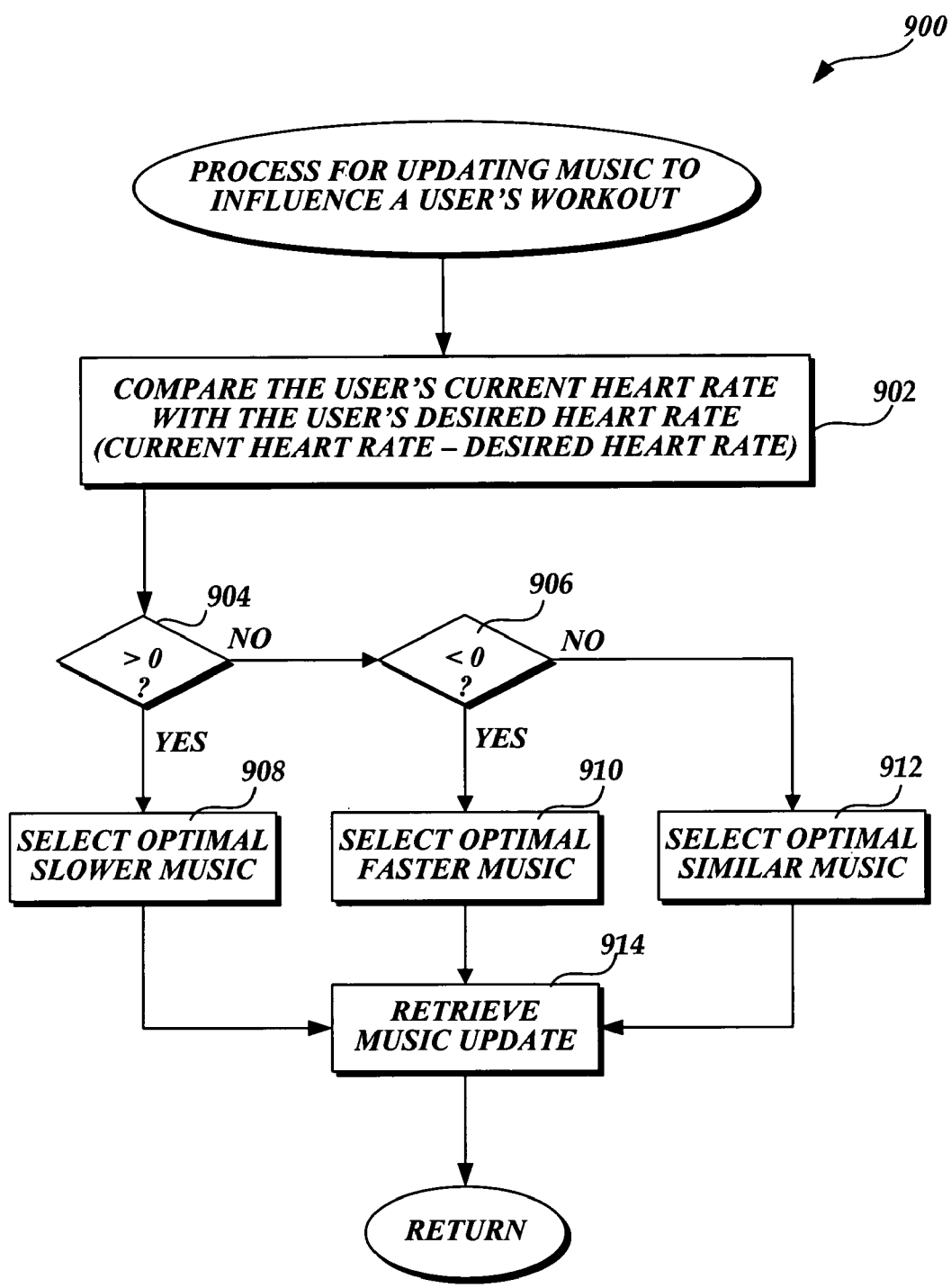
FIG. 9 is a flow diagram illustrating an exemplary process for updating music to influence a user's workout, suitable for use in FIG. 4.

Regardless of where the MPTrain software 318 obtains the current heart rate and movement speed readings of the user 102 from, the MPTrain software 318 uses the current heart rate and movement speed readings of the user 102 to determine how to update the music being played for the user 102. In exemplary embodiments of the invention, the MPTrain software 318 performs a music update function 324 to identify the next music to be played or adjust features in the music being currently played. The updated music 110 then is played to help the user 102 achieve the desired exercise pattern by influencing the movement speed of the user 102, hence, the heart rate of the user 102. FIG. 9 illustrates an exemplary implementation of the music update function 324 and will be discussed in detail below in Section IV.

Upon identifying the next music piece to play, in an exemplary embodiment of the invention, the MPTrain software 318 retrieves the music piece from a music library such as a digital music library ("DML") 326. The DML 326 may store music specific to the user 102 or may store music for multiple users. In embodiments of the invention, the DML 326 may contain not only music pieces but also additional information about each music piece, such as its beat and average energy.

The MPTrain software 318 may also log information (e.g., heart rate, number of steps per minute, and music being played) concerning the current exercise session of the user 102 in a log database 328. In embodiments of the invention, the MPTrain software 318 may consult previous log entries in the log database 328 for the user 102 in deciding how to update music in a way that is specifically helpful to the user 102.

In embodiments of the invention, the DML 326 and/or the log database 328 may reside locally on the computing device 106 or remotely in a storage place that the computing device 106 may have access to through network communication. Upon retrieving the music piece, the MPTrain software 318 interfaces with a media player 330, such as an MP3 player, to reproduce the music piece accordingly.

Figure 10:
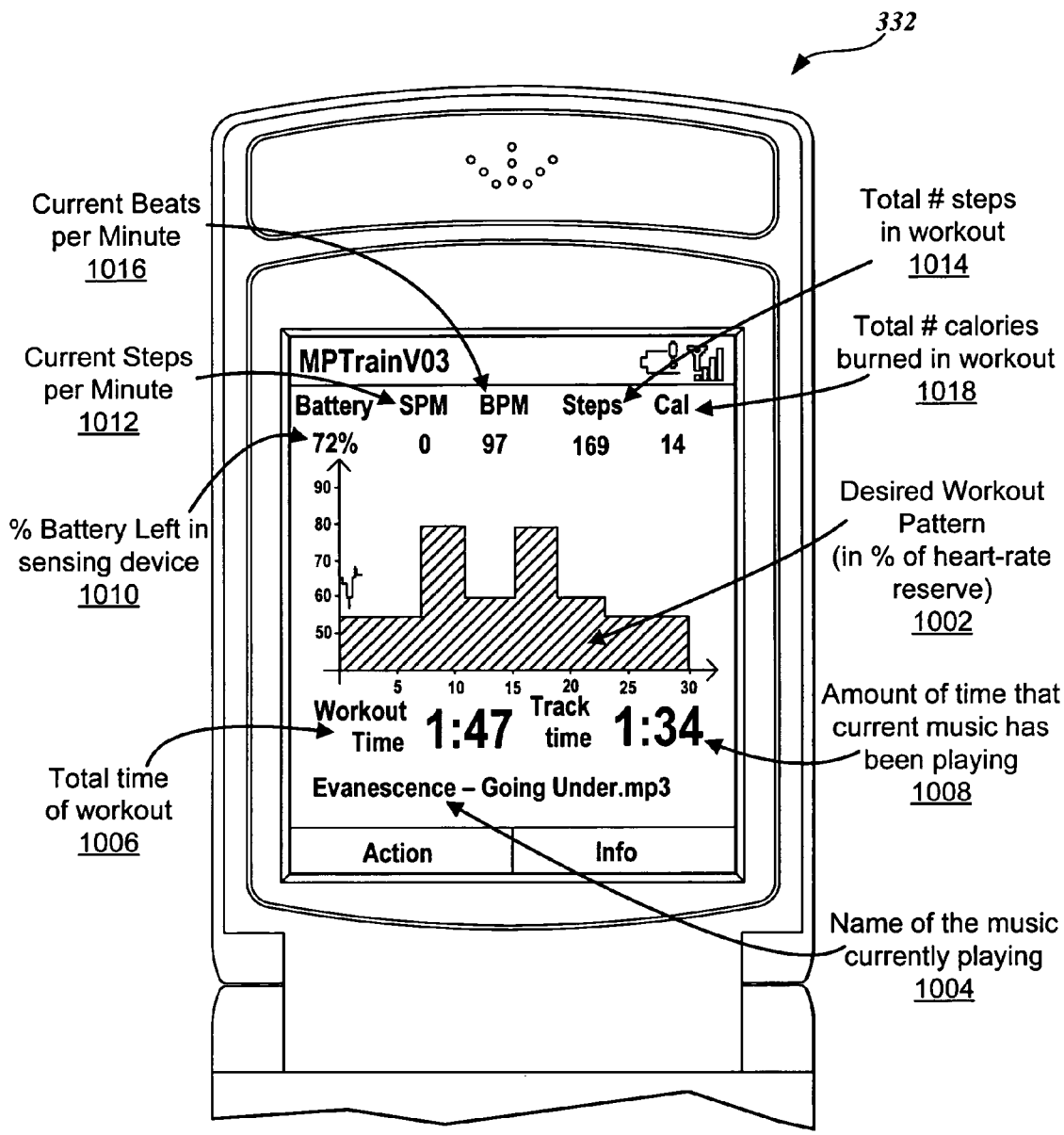
FIG. 10 is a pictorial diagram illustrating an exemplary user interface for an exemplary MPTrain system.
Figure 11:
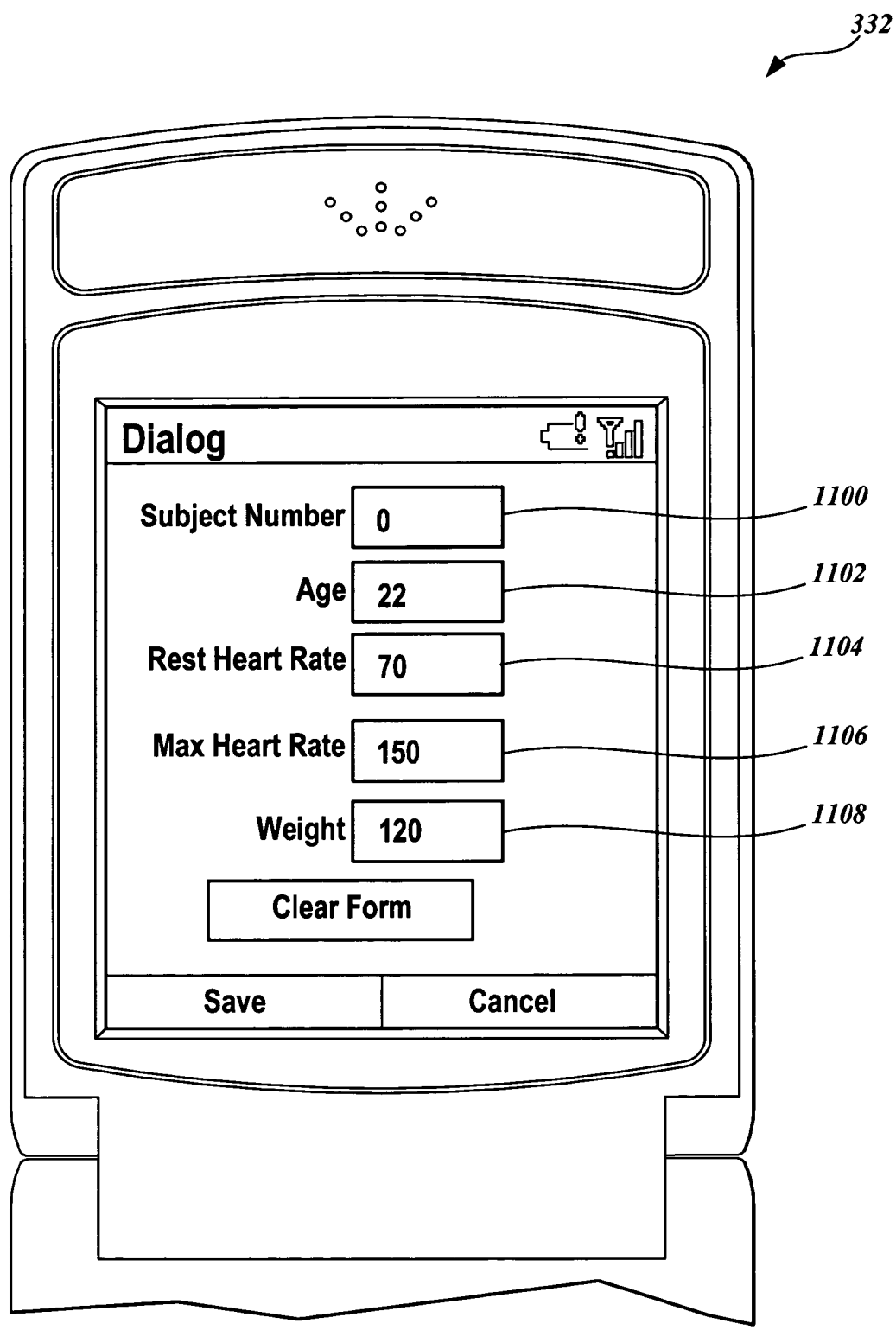
FIG. 11 is a pictorial diagram illustrating another exemplary user interface for an exemplary MPTrain system.

In some embodiments of the invention, the computing module 304 may further include a user interface 332. The user interface 332 may present current information about the MPTrain system. Such information may include, but not limited to, the current heart-rate and/or movement speed of the user 102, the progress of the user 102 within the selected exercise pattern, the music being played, sound volume. The user interface 332 may also allow the user 102 to enter desired exercise pattern, set parameters, and/or change music. FIGS. 10-11 illustrate an exemplary implementation of the user interface 332 and will be described in detail below in Section V.

In one embodiment of the invention, the MPTrain software 318 is implemented as a Windows® Mobile application, with all its functionalities (e.g., sensor data reception, data analysis, display, storage, music update, and playback) running simultaneously in real-time on the computing device 106.

Figure 4:
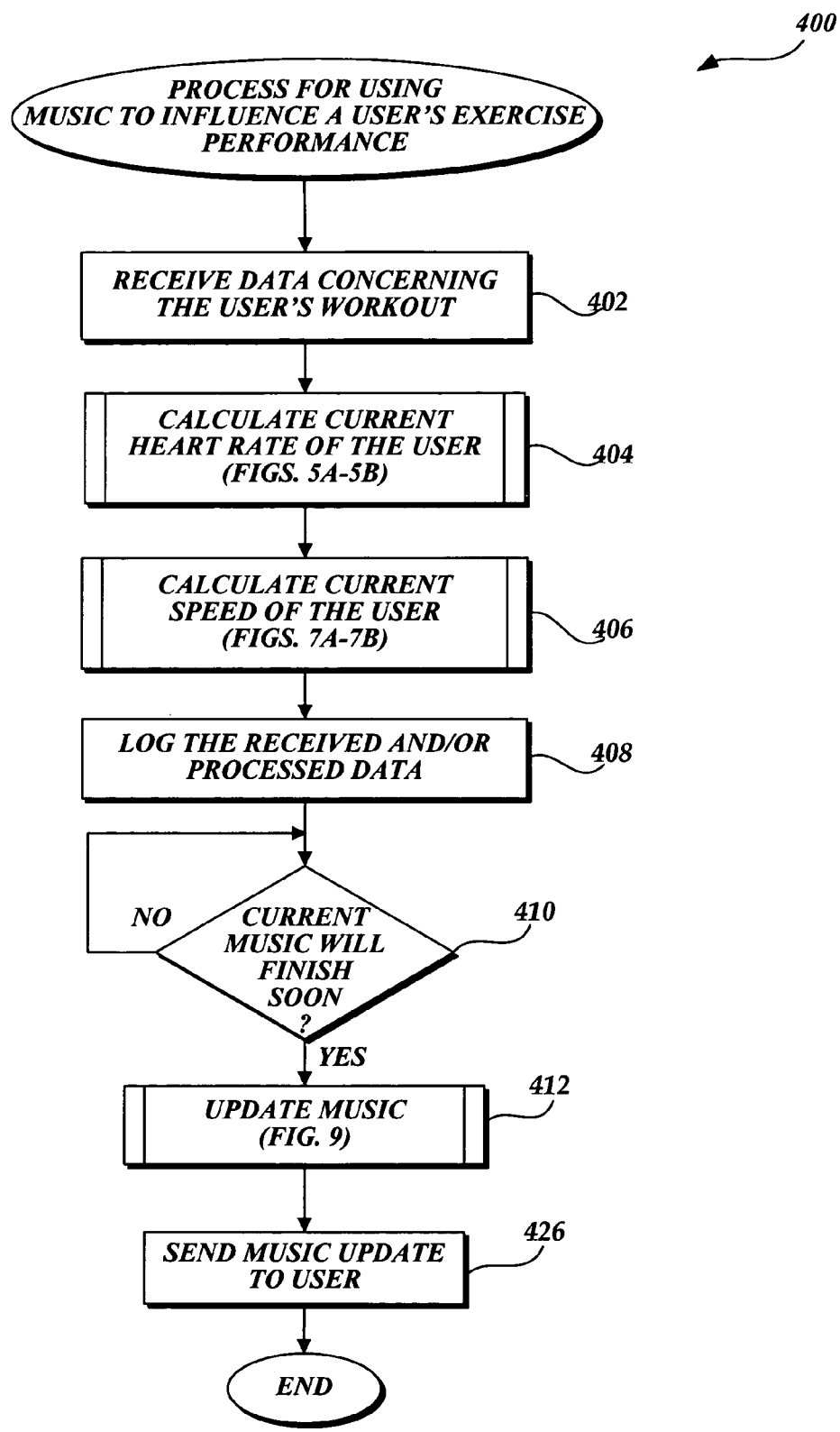
FIG. 4 is a flow diagram illustrating an exemplary process for using music to influence a user's exercise performance.

FIG. 4 is a flow diagram illustrating an exemplary process 400 that utilizes music to help a user achieve desired exercising goals during a workout session. The process 400 is described with reference to the usage scenario 100 illustrated in FIG. 1, the exemplary hardware 200 illustrated in FIG. 2, and the exemplary MPTrain architecture 300 illustrated in FIG. 3. As shown in FIG. 1, when the user 102 exercises, the user 102 wears sensors 104 and carries the computing device 106 that can function both as a personal computer and as a personal music player. The user 102 listens to music provided by the computing device 106 while exercising. In exemplary embodiments of the invention, the process 400 is implemented by the MPTrain software 318 (FIG. 3) that is part of the computing module 304 incorporated in the computing device 106.

While the user 102 is exercising, the sensors 104 capture the sensor data 108 and forward the sensor data 108 to the computing device 106. Thus, the process 400 receives data concerning the workout of the user 102. See block 402. As noted above, the sensor data 108 may include physiological data indicating, for example, the current heart rate of the user 102 as well as the current movement speed of the user 102. In some embodiments of the invention, the data received by the process 400 may already contain current heart rate and movement speed readings of the user 102. In other embodiments of the invention, the data received by the process 402 may need to be processed to obtain the desired information. In the latter situation, the process 400 proceeds to calculate the current heart rate of the user 102. See block 404. That is, the process 400 executes the heart rate computation function 320 illustrated in FIG. 3. The process 400 may also need to calculate the current movement speed of the user 102. See block 406. That is, the process 400 executes the speed computation function 322 illustrated in FIG. 3.

In some embodiments of the invention, the process 400 stores the received and/or the processed data concerning the workout session of the user 102, such as in the log database 302 illustrated in FIG. 3. See block 408.

In exemplary embodiments of the invention, shortly (e.g., 10 seconds) before the music that is currently being played to the user 102 finishes, the process 400 initiates the music update function 324 illustrated in FIG. 3. Therefore, as shown in FIG. 4, the process 400 checks whether the music currently being played will finish soon. See decision block 410. If the answer is No, the process 400 does not proceed further. If the answer is YES, the process 400 executes the music update function 324. See block 412. The process 400 then sends any music update to the media player 330 for playback (FIG. 3). See block 426. The process 400 then terminates. In another exemplary embodiment of the invention, MPTrain alters the playback speed with which the songs are being reproduced without affecting their pitch to better suit the exercise needs of the user.

II. Extracting Information from Raw Sensor Data

As noted above while describing the overall architecture of the MPTrain system, the sensor data 108 provided by the sensors 104 may include raw sensor signals that need to go through data analysis in order to extract desired information. In embodiments of the invention, such desired information may include the current heart rate and/or movement speed (pace) of the user 102. The process of analyzing the sensor data 108 containing raw sensor signals to extract desired information may be performed by the sensing device 202, the computing device 106, or another device that can communicate with the sensors 104 and the computing device 106 via the network 208.

In an exemplary embodiment of the invention, the sensor data 108 provided by the sensing module 302 include raw ECG and acceleration signals. Such sensor data 108 are then continuously transmitted over to the computing device 106 via the network 208. From this raw data stream, the MPTrain software 318 computes the current heart rate (e.g., in beats per minute) and movement speed (e.g., in steps per minute) of the user 102.

A. Heart Rate Computation

As known by those of ordinary skill in the art, ECG is a graphic record of a heart's electrical activity. It is a noninvasive measure that is usually obtained by positioning electrical sensing leads (electrodes) on the human body in standardized locations. In an exemplary embodiment of the invention, a two-lead ECG is positioned on the torso of the user 102, either via a chestband or with two adhesive electrodes. The current heart rate of the user 102 is then computed from the collected raw ECG signals using a heart rate detection algorithm described below.

Figure 5A:
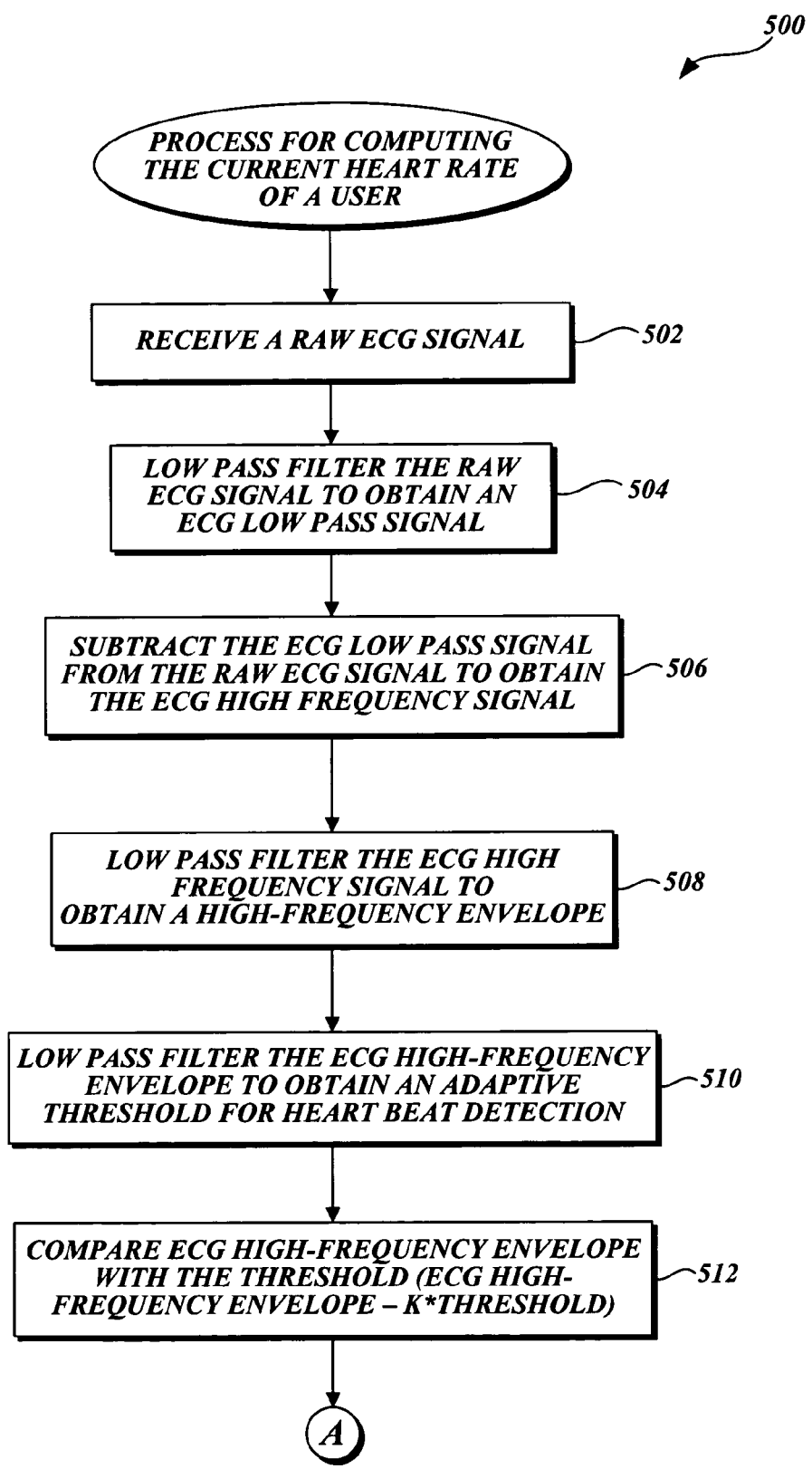
FIGS. 5A-5B is a flow diagram illustrating an exemplary process for computing the current heart rate of a user, suitable for use in FIG. 4.
Figure 5B:
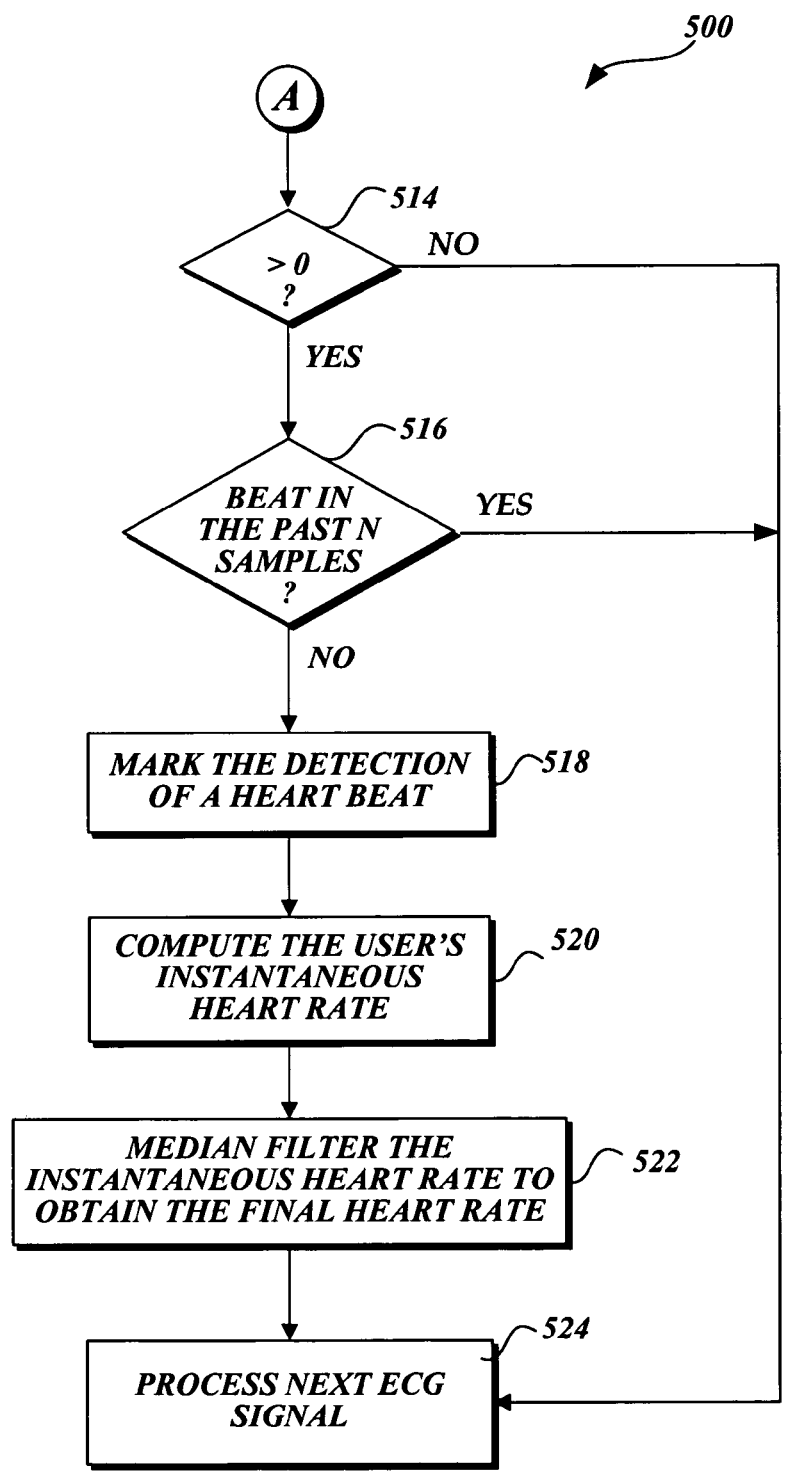

FIGS. 5A-5B provide a flow diagram illustrating an exemplary process 500 for computing the current heart rate of the user 102 from the raw ECG signals included in the sensor data 108. As shown in FIG. 5A, the process 500 starts upon receiving a raw ECG signal. See block 502. The raw ECG signal is then low-pass filtered to obtain an ECG low pass signal (ECGLowpassSignal). See block 504. As known by those skilled in the art, a low pass filter allows frequencies lower than a certain predetermined frequency level to pass while blocking frequencies higher than the predetermined frequency level. The process 500 then computes the high-frequency component of the ECG signal, named ECGHighFreqSignal, by subtracting the ECGLowpassSignal from the raw ECG signal. See block 506. The process 500 then computes a high-frequency envelope, named ECGHighFreqEnv, by low-pass filtering the ECGHighFreqSignal. See block 508. Next, the process 500 proceeds to determine an adaptive threshold for heart beat detection, named ECGThreshold, by applying a low-pass filter with very low pass frequency to the ECGHighFreqEnv. See block 510. The low-pass filtered signal from the ECGHighFreqEnv accounts for the variance in the ECG raw signal and therefore constitutes an adaptive threshold. The threshold is adaptive because its value depends on the current value of the ECG signal and therefore changes over time.

The process 500 then compares the ECG high frequency envelope with the adaptive threshold. See block 512. In an exemplary implementation, the process 500 multiplies the adaptive threshold with a positive integer K, for example, three. The process 500 then subtracts the multiplication result from the ECG high frequency envelope. The process 500 then determines if the result of the subtraction is positive. See decision block 514 (FIG. 5B). If ECGHighFreqEnv>K*ECGThreshold, the process 500 determines if a beat has been detected in the past N samples of ECG signals (where N is typically 10). See decision block

516. If the answer to decision block 516 is NO, the process 500 marks that a new heart beat has been detected. See block 518. If the answer to decision block 514 is NO, or the answer to decision block 516 is YES, the process 500 proceeds to process the next ECG signal. See block 524.

Upon deciding that a new heart beat has been detected, the process 500 proceeds to compute the instantaneous (actual) heart rate of the user 102, that is, the user's heart-rate at each instant of time. See block 520. In an exemplary implementation, the process 500 computes the instantaneous heart rate $HR_i$ using the following formula:

$$HR_i = (\text{int})\frac{60.0 * SamplingRate}{\#SamplesBetweenBeats}.$$

In an exemplary implementation of the process 500, the value of the $HR_i$ is assumed to be in a range of about 30 and about 300; the SamplingRate is about 300 Hz; and the #SamplesBetweenBeats is the number of ECG signals received since the last detected heart beat.

Upon computing the $HR_i$, the process 500 applies a median filter to the $HR_i$ to obtain the final heart-rate reading of the user 102. See block 522. As known by those of ordinary skill in the art, median filtering is one of common nonlinear techniques used in signal processing. It offers advantages such as being very robust, preserving edges, and removing impulses and outliers. The process 500 then proceeds to process the next signal. See block 524.

Figure 6:
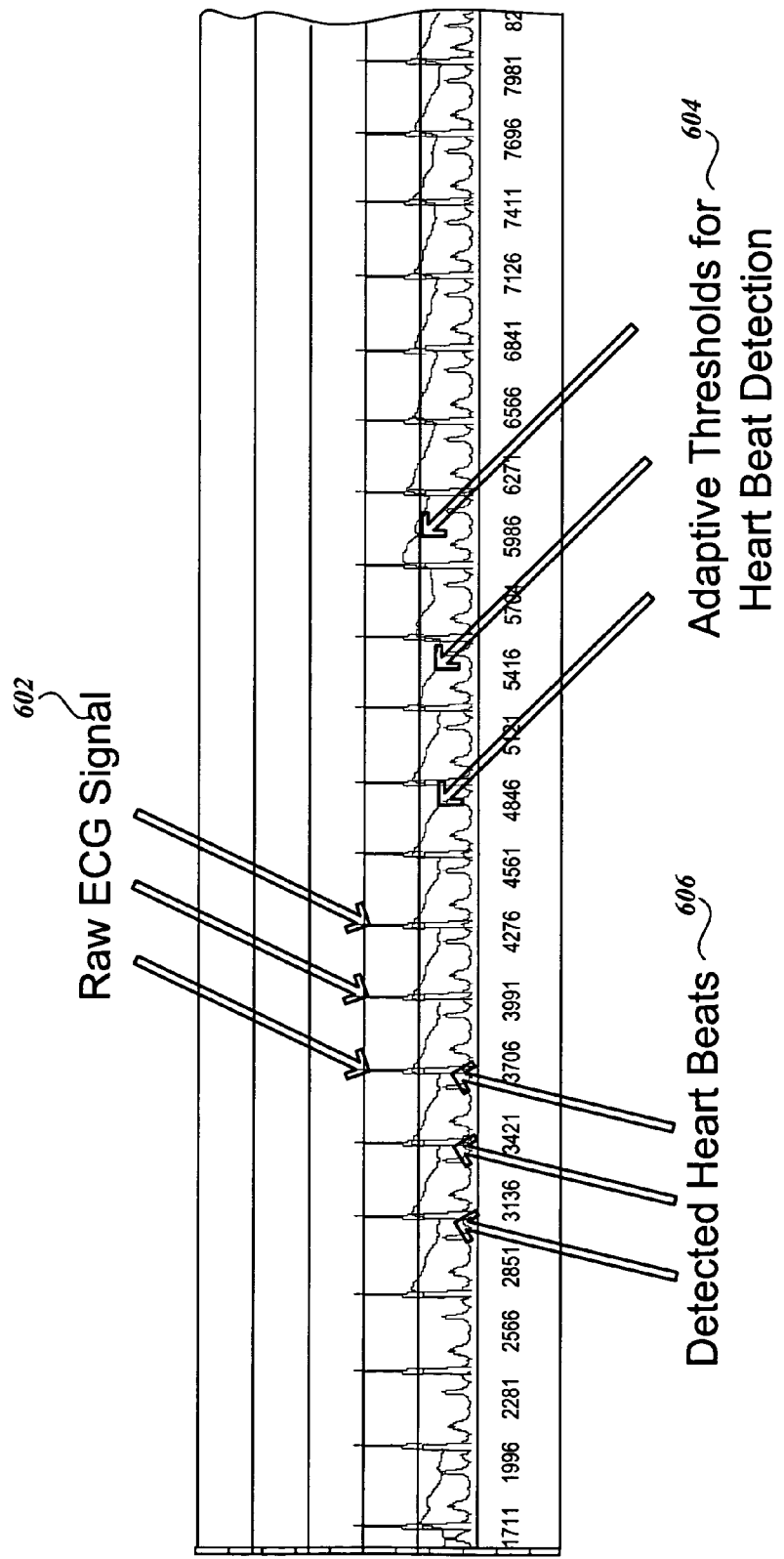
FIG. 6 is a data diagram illustrating exemplary electrocardiogram ("ECG") signals and the data extracted from the ECG signals.

FIG. 6 illustrates exemplary raw ECG signals 602, along with their corresponding adaptive thresholds for heart beat detection 604 and the detected heart beats 606 that are computed using the exemplary process 500 described above.

B. Running Pace (Speed) Computation

Embodiments of the invention measure the movement pace of the user 102 by determining the number of steps that the user 102 is taking per minute ("SPM"). Exemplary embodiments of the invention measure the SPM by using the sensor data 108 gathered from the accelerometer 306 (FIG. 3). In embodiments of the invention, the accelerometer 306 can be multiple-axis, such as two-axis (so to measure a user's movement in X and Y dimensions) or three-axis (so to measure a user's movement in X, Y, and Z dimensions).

Figure 7A:
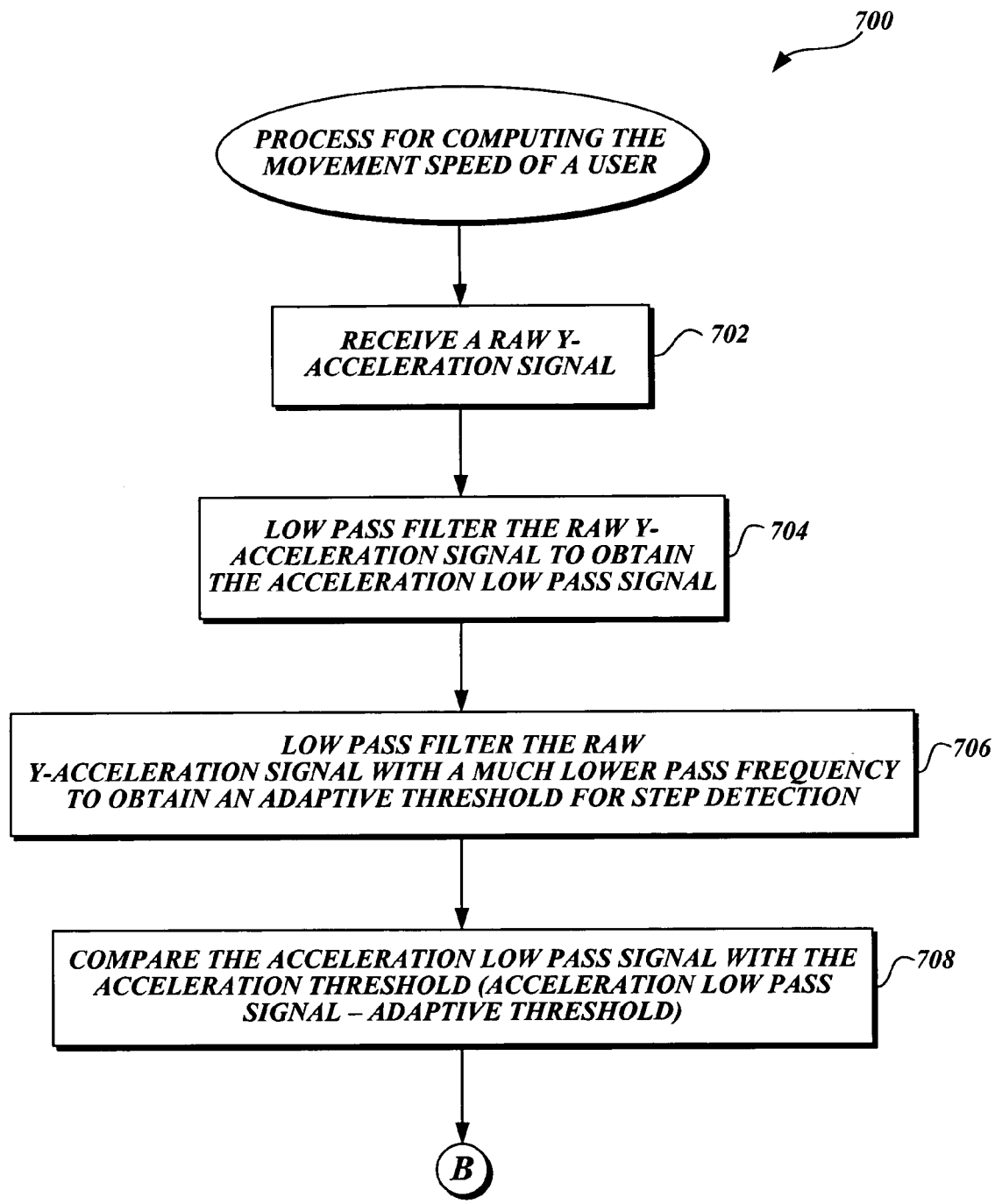
FIGS. 7A-7B is a flow diagram illustrating an exemplary process for computing the movement speed of a user, suitable for use in FIG. 4.
Figure 7B:
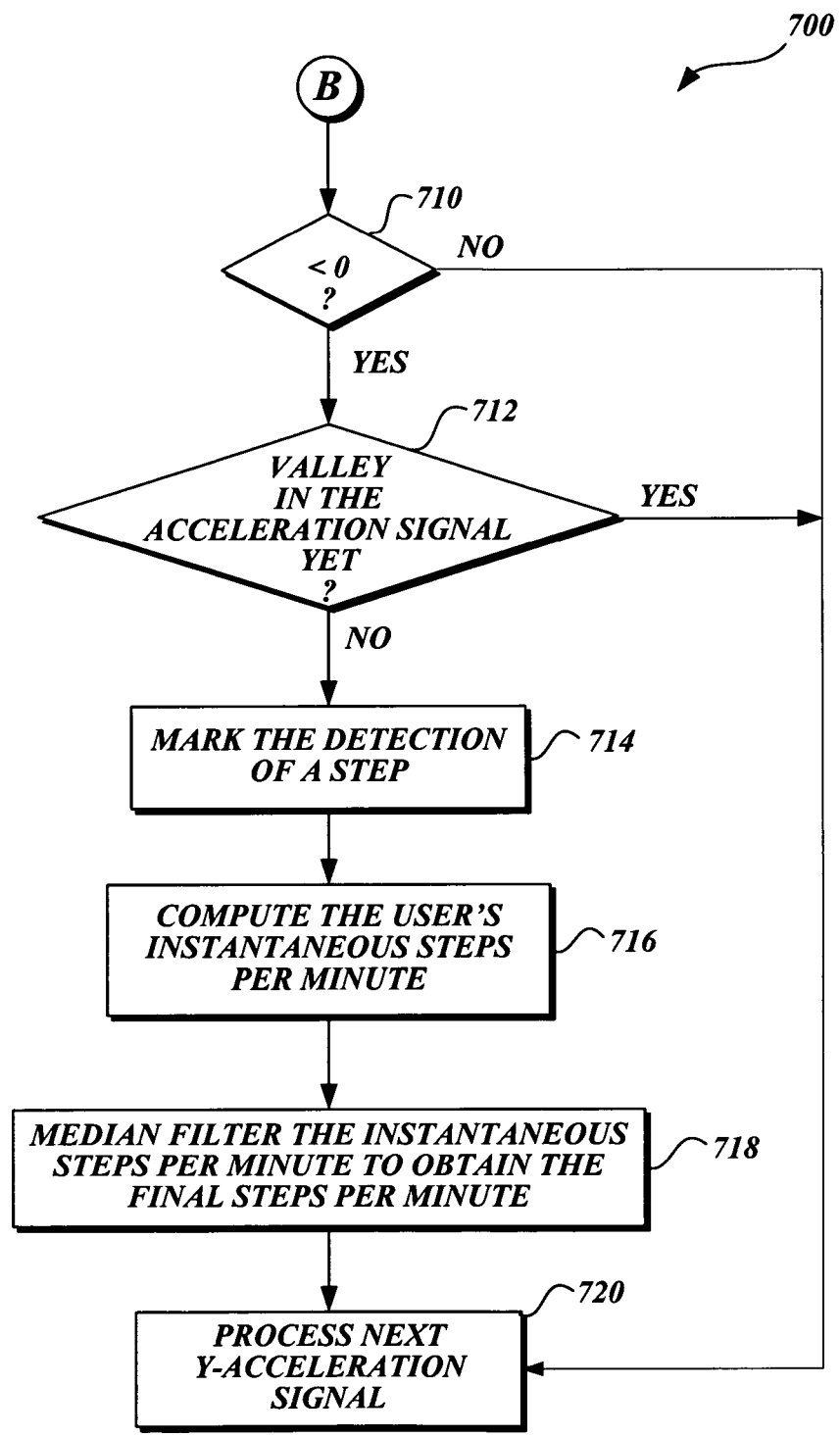

FIGS. 7A-7B provide a flow diagram illustrating an exemplary process 700 for computing the current movement speed of the user 102 using the sensor data 108 gathered from the accelerometer 306. In the illustrated implementation, the exemplary process 700 only uses vertical acceleration (movement of the user 102 in Y dimension) data collected from the accelerometer 306.

As shown in FIG. 7A, the process 700 starts upon receiving a raw Y-acceleration signal. See block 702. The raw Y-acceleration signal is then low-pass filtered to obtain an acceleration low pass signal (AccLowpassSignal). See block 704. Another low-pass filter with much lower pass frequency is then applied to the same raw Y-acceleration signal to generate an adaptive threshold for step detection (AccThreshold). See block 706. The acceleration low pass signal is then compared to the adaptive threshold for step detection, for example, by subtracting the adaptive threshold for step detection from the acceleration low pass signal. See block 708. The process 700 then determines if the acceleration low pass signal is lower than the acceleration threshold. See decision block 710 (FIG. 7B). If the answer is YES, the process 700 determines if the raw Y-acceleration signal has had a valley yet. See decision block 712. When the user is walking or running, the Y-acceleration signal follows a wave pattern, where each cycle of the wave corresponds to a step. Therefore, by automatically detecting the valleys in the signal, one can detect the number of steps that the user has taken. If the answer to the decision block 712 is NO, the process 700 marks that a step is detected. See block 714. If the answer to the decision blocks 710 is NO or the answer to the decision block 712 is YES, the process 700 proceeds to process the next Y-acceleration signal. See block 720.

After detecting a step, the process 700 proceeds to compute the instantaneous SPM ($SPM_i$) for the user 102, that is, the number of steps per minute that the user has taken at the instant of time t=i. See block 716. In an exemplary implementation, the process 700 computes the $SPM_i$ using the following formula:

$$SPM_i = (\text{int})\frac{60.0 * SamplingRate}{\#SamplesSinceLastStep}.$$

In an exemplary implementation of the process 700, the SamplingRate for the acceleration signal is about 75 Hz and the #SamplesSinceLastStep is the total number of data samples since the last detected step.

After computing the $SPM_i$, the process 700 applies a median filter to the $SPM_i$ to obtain the final number of steps per minute, SPM. See block 718. The process 700 then moves to process the next raw Y-acceleration signal. See block 720.

Figure 8:
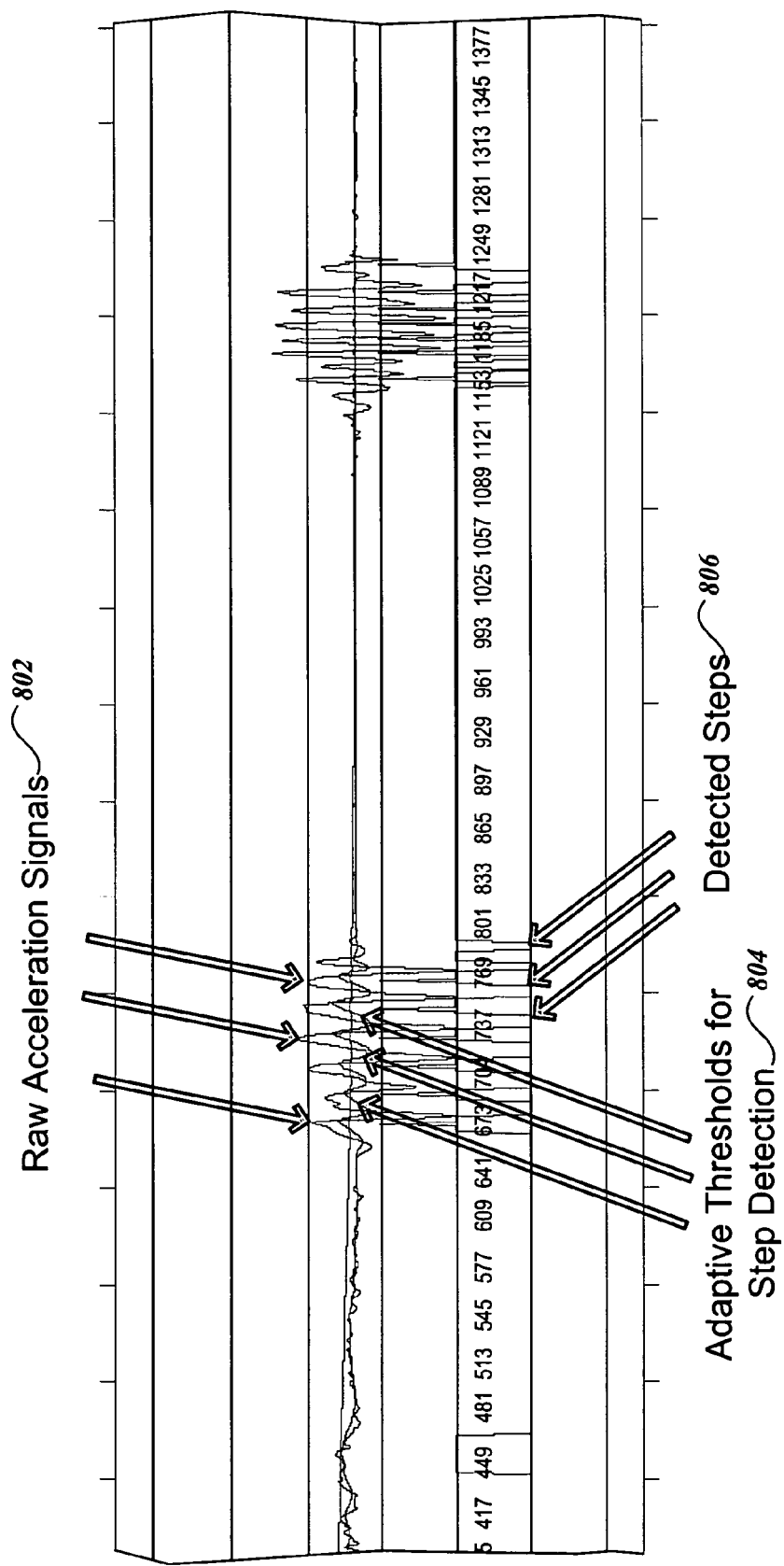
FIG. 8 is a data diagram illustrating exemplary acceleration signals and data extracted from the acceleration signals.

FIG. 8 illustrates exemplary raw acceleration signals 802, together with their corresponding adaptive thresholds for step detection 804 and the detected steps 806 that are computed using the exemplary process 700 described above.

III. Exemplary Features Used for Characterizing a Music Piece

Exemplary embodiments of the invention characterize a music piece with the following exemplary features:

1. Average Energy. When working with a stereo audio signal, there are two lists of discrete values-one for each channel a(n) and b(n)—such that a(n) contains the list of sound amplitude values captured every S seconds for the left channel and b(n) the list of sound amplitude values captured every S seconds for the right channel. The audio signal is typically sampled at 44,100 samples per second (44.1 KHz). Assuming a buffer includes 1024 samples for computing the instantaneous sound energy, E(i), which is given by $$E(i) = \sum_{k=t0}^{t0+1024} a(k)^2 + b(k)^2.$$

Then the average energy, <E>, of the sound signal is given by $$<E> = \frac{1024}{N}\sum_{i=0}^{N}(a(i)^2 + b(i)^2),$$

where N is typically 44,100 (i.e., one second of music). It has been experimentally shown that the music energy in the human ear persists for about one second, and hence this N value. Because there are 43 instantaneous energies in a second (1024*43>=44100 or 43~44100/1024), the average energy <E> of a music piece thus can be expressed as:

$$<E> = \frac{1}{43} \sum_{i=0}^{43} E(i).$$

2. Variance in the Energy. In exemplary embodiments of the invention, the variance in the energy of the sound is computed as the average of the difference between the instantaneous energy and the average energy over a certain time interval. The variance in the energy can be expressed as $$<VE> = \frac{1}{N} \sum_{i=0}^{N} (E(i) - <E>)^2,$$

where N is integer (typically 43 to cover one second of music).

3. Beat. Typically, beat of a music piece corresponds to the sense of equally spaced temporal units in the musical piece. The beat of a music piece can be defined as the sequence of equally spaced phenomenal impulses that define a tempo for the music piece. There is no simple relationship between polyphonic complexity—the number and timbres of notes played at a single time—in a music piece and its rhythmic complexity or pulse complexity. For example, the pieces and styles of some music may be timbrally complex, but have a straightforward, perceptually simple beat. On the other hand, some other music may have less complex musical textures but are more difficult to understand and define rhythmically.

A myriad of algorithms exists for automatically detecting beat from a music piece. Most of the state-of-the art algorithms are based on a common general scheme: a feature creation block that parses the audio data into a temporal series of features which convey the predominant rhythmic information of the following pulse induction block. The features can be onset features or signal features computed at a reduced sampling rate. Many algorithms also implement a beat tracking block. The algorithms span from using Fourier transforms to obtain main frequency components to elaborate systems where banks of filters track signal periodicities to provide beat estimates coupled with its strengths. A review of automatic rhythm extraction systems is contained in: F. Gouyon and S. Dixon, "A Review of Automatic Rhythm Description Systems," *Computer Music Journal* 29(1), pp. 34-54, 2005. Additional references are: E. Scheirer, "Tempo and beat analysis of acoustic musical signals," *J. Acoust. Soc. Amer.*, vol. 103, no. 1, pp. 588, 601, January 1998; M. Goto and Y. Muraoka, "Music understanding at the beat level: Real-time beat tracking of audio signals," in *Computational Auditory Scene Analysis*, D. Rosenthal and H. Okuno, Eds., Mahwah, N.J.: Lawrence Erlbaum, 1998, pp. 157-176; J. Laroche, "Estimating tempo, swing and beat locations in audio recordings," in *Proc. Int. Workshop on Applications of Signal Processing to Audio and Acoustics(WASPAA)*, Mohonk, N.Y., 2001, pp. 135-139; J. Seppänen, "Quantum grid analysis of musical signals," in *Proc. Int. Workshop on Applications of Signal Processing to Audio and Acoustics (WASPAA)* Mohonk, N.Y., 2001, pp. 131-135; and J. Foote and S. Uchihashi, "The beat spectrum: A new approach to rhythmic analysis," in *Proc. Int. Conf. Multimedia Expo.*, 2001. Any of the algorithms described in these articles can be used to automatically determine the beat of a music piece in the DML 326.

Embodiments of the invention characterize a music piece by ranges of beats rather than the exact beat. For example, an exemplary embodiment of invention groups together music pieces whose beats are in the range of about 10-30 beats per minute ("bpm"), about 31-50 bpm, about 51-70 bpm, about 71-100 bpm, about 101-120 bpm, about 121-150 bpm, about 151-170 bpm, etc. There are a few reasons for characterizing a music piece by a range of beats rather than the exact beat. For example, none of the existing beat detection algorithms works perfectly on every music piece. Defining a range of beats rather than depending on the exact beat increases the robustness of an MPTrain system to errors in the existing beat detection algorithms. In addition, users typically respond in a similar way to music pieces with similar (but not necessarily identical) beats. For example, music pieces in the about 10-30 bpm range are usually perceived as "very slow" music and tends to induce a similar response in the users.

4. Volume. Exemplary embodiments of the invention may also take into account the volume at which a music piece is being played. It is presumed that the higher the volume of a music pieces, the faster the user 102 may move.

In exemplary embodiments of the invention, the exemplary musical features described above are computed per segment of a music piece rather than for the entire length of the music piece. For example, one embodiment of the invention divides a music piece into segments of about 20 seconds in length. Consequently, each music piece in the DML 326 comprises a collection of N vectors ($v_i$, i=1 ... N) characterizing the music piece, where N equals the length of the music piece in seconds divided by 20. Each of the N vectors, $v_i$=(<E>,<VE>,beat), contains the average energy, variance in the energy, and beat values for the corresponding segment of the music piece.

IV. Updating Music for a User During the User's Workout

One of the invention's goals is to use music to keep the user 102 on track with his or her exercise objectives during an exercise routine. The music update function 324 (FIG. 3) achieves such a purpose by automatically modifying features of the music piece currently playing or selecting a new music piece to play so to induce the user 102 to speed up, slow down, or maintain current pace of workout.

An exemplary embodiment of the invention monitors the current heart rate and movement speed of the user 102. It then computes the deviation, $\Delta HR(t)$, of the current heart rate, $HR_c(t)$, from the desired heart rate, $HR_d(t)$, at a given moment t (as defined by the exercise routine of the user 102). Depending on the value of $\Delta HR(t)$, the embodiment of the invention determines whether to increase, decrease, or maintain the current movement speed of the user 102. For example, if $HR_c(t)$=100 and $HR_d(t)$=130, the embodiment of the invention may determine that the user 102 needs to increase movement speed such that the heart rate of the user 102 may increase and come closer to the desired heart rate.

An exemplary embodiment of the invention assumes that the higher the average energy, the variance in the energy, the beat, and/or the volume of a music piece, the faster the user 102 may exercise as a result of listening to the musical piece. It therefore assumes a positive correlation between the desired $\Delta HR(t)$ and the difference between the current feature vector $v_c(t)$=(<E>,<VE>,beat) of the music being played and the desired feature vector $V_d(t)$=(<E>,<VE>,beat). That is, $\Delta HR(t) \propto \Delta v(t) = v_c(t) - v_d(t)$. Therefore, in order to increase the current heart rate of the user 102, an exemplary embodiment of the invention may increase the beat and/or volume of the current music piece. Alternatively, it may choose a new music piece with a higher value of (<E>,<VE>,beat) such that the current movement speed of the user 102 increases and therefore his/her heart rate increases correspondingly.

FIG. 9 is a flow diagram illustrating an exemplary process 900 for updating music to help a user achieve desired exercise performance. In exemplary embodiments of the invention, the process 900 determines whether the user 102 needs to speed up, slow down, or maintain the speed of the exercise by deciding whether the user 102 needs to increase, decrease, or maintain his or her current heart rate. Thus, the process 900 compares the current heart rate of the user 102 with the desired workout heart rate of the user 102, for example, by subtracting the desired heart rate from the current heart rate. See block 902. In an exemplary embodiment of the invention, the heart rate is represented by heart beats per minute. The desired heart rate is the maximum allowed heart rate for the user 102 at a given moment in a specific workout routine.

The process 900 then proceeds differently according to whether the result of the subtraction is positive (see decision block 904), negative (see decision block 906), or being zero. If the current heart rate is greater than the desired heart rate, the process 900 proceeds to select an optimal slower music piece. See block 908. If the current heart rate is slower than the desired heart rate, the process 400 proceeds to select an optimal faster music piece, hoping to boost up the movement speed of the user 102. See block 910. Otherwise, the current heart rate is equivalent to the desired heart rate, the process 900 proceeds to select an optimal similar music piece. See block 912. The process 900 then retrieves the selected music piece from the DML 326 (FIG. 3). See block 914. The process 900 then returns. In embodiments of the invention, "optimal" means that the selected music is the best candidate for possibly producing the desired effect on the user 102.

In an exemplary embodiment of the invention, the illustrated process 900 determines the next music piece to be played by identifying a song that (1) hasn't been played yet and (2) has a tempo (in beats per minute) similar to the current gait of the user 102. If necessary, the process 900 may instead choose a faster (or slower) track to increase (or decrease) the user's heart-rate in 102 in an amount inversely related to the deviation between the current heart-rate and the desired heart-rate from the preset workout. For example, if the user's current heart rate is at 55% of the maximum heart rate, but the desired heart rate at that point is at 65%, exemplary embodiments of the invention will find a music piece that has faster beat than the one currently being played. Yet, in considering the physical limitations of the user 102, the MPTRain system may select a music piece with a beat only slightly higher (within a 15-20% range) than the current one so to allow the user 102 to make a gradual change in movement speed. In one exemplary embodiment of the invention, the music selection algorithm learns in real-time the mapping between musical features and the user's running pace from the history of past music/pace pairs.

In another exemplary embodiment of the invention, the music selection algorithm includes other criteria in addition to the ones mentioned in the previous paragraph, such as the duration of the musical piece and the position of the user in the workout routine. For example, if the user is 1 minute away from a region in the workout that will require him/her to speed up (e.g. going from 60% of maximum heart-rate to 80% of maximum heart-rate), the music selection algorithm will find a song whose tempo will induce the user to start running faster. In the more general case, the algorithm computes the mean error over the entire duration of each song between the heart-rate that that particular song will induce in the user and the desired heart-rate based on the ideal workout. The algorithm will choose the song with the smallest error as the song to play next.

The illustrated process 900 selects a new music piece according to the difference between the current heart rate and the corresponding desired heart rate of the user 102. In some embodiments of the invention, alternatively, depending on the difference between the current heart rate and the desired heart rate of the user 102, instead of selecting a new music piece accordingly, the process 900 may modify the features of the music piece that is currently being played so that the features of the current music can be adjusted to speed up, slow down, or remain the same, so to influence the movement speed of the user 102 accordingly, and therefore the heart rate of the user 102.

Even more, other embodiments of the invention may first try to change the features of the music piece currently being played, before changing to another music piece. In reality, there are limitations to how much a music feature can be changed without affecting too much the quality of the music piece. For example, one is limited in changing the beat of a music piece without affecting its pitch (approximately from 0.9 to 1.1). Therefore, when modifying the features of the current music piece is not sufficient, some embodiments of the invention may shift to change to a new music piece, for example, by using a fade out/in feature.

Besides the current heart rate and movement speed of the user 102, embodiments of the invention may also consider additional information specifically related to the user 102 when deciding how to update music for the user 102. Such information includes:

1. Factors such as fatigue and emotional responses of the user 102 to certain music pieces that may have an impact on how much a music piece affects the user 102. Embodiments of the invention may adapt to these factors. For example, as noted above when describing the exemplary MPTrain architecture 300, embodiments of the invention may keep track of the history of music pieces played in past exercise sessions and the responses (e.g., heart rate and movement speed) they caused in the user 102. Such historic and individual-specific information can therefore be used to predict the effect that a particular music piece may have in the particular user 102. Embodiments of the invention can thus customize the music update functionality 324 specifically for the user 102. Similarly, by keeping track of the amount of time that the user 102 has been exercising and the movement speed and heart rate of the user 102, embodiments of the invention can determine the level of tiredness of the user 102 and predict how effective a music piece would be in influencing the movement speed of the user 102.

2. Additional factors specific to the user 102, such as stress levels of the exercise, general level of physical conditioning, physical location of the user, weather conditions, and health of the user 102, that may also have an impact on the effectiveness of the music piece on the user 102.

3. Different impacts of features of a music piece on the user 102. Each of the exemplary features used to characterize a music piece, e.g., <E>, <VE>, beat, and volume, may have a different impact on the user 102. Therefore embodiments of the invention assign a feature vector with weights such as $\alpha, \beta, \lambda$, so the feature vector, $v(t)=(\alpha<E>, \beta<VE>, \lambda Beat)$, may incorporate user-specific data. The weights $\alpha, \beta, \lambda$ may be empirically determined from data via machine learning and pattern recognition algorithms.

4. User feedback. For example, the user explicitly requesting MPTrain to change songs by pressing one button on the mobile phone. MPTrain keeps track of these interactions and incorporates the user's feedback in the song selection algorithm.

In other exemplary embodiments of the invention, the MPTrain monitors actions of the user 102 and learns from them by storing the information in the log database 328 and using the information to provide music update 110 that is suitable to the user 102. Thus, as the user 102 interacts with the MPTrain, its music update function 324 become progressively better suited for the particular user 102. As a result, the MPTrain acts as a virtual personal trainer that utilizes user-specific information to provide music that encourages the user 102 to accelerate, decelerate, or keep the current movement speed.

V. Exemplary User Interface

FIG. 10 is a screenshot of an exemplary MPTrain user interface 332 (FIG. 3). The solid graph in the center of the window depicts a desired workout pattern 1002 for the user 102. As shown, the desired workout pattern 1002 includes a graph of the desired workout heart rate (y-axis)—as a percentage of the heart rate reserve for the user 102—over time (x-axis). Heart rate reserve is the maximum allowed heart rate—resting heart rate. The maximum allowed heart rate is typically computed as 220-age. The depicted workout pattern 1002 contains a warm-up period (left-most part of the graph), with desired heart rate at 35% of the maximum heart rate, followed by successively more intense exercising periods (desired heart rates at 80, 85, and 90% of the maximum heart rate) and ended by a cool-down phase (right-most part of the graph), with desired heart rate at 40% of the maximum heart rate. In embodiments of the invention, when an MPTrain is in operation, a line graph (not shown) may be superimposed to the desired workout pattern 1002 to depict the actual performance of the user 102. The line graph feature may allow the user 102 to compare in real-time his/her performance with the desired performance.

In embodiments of the invention, through the user interface 332, at any instant of time, the user 102 can check how well the user is doing with respect to the desired exercise level, modify the exercising goals and also change the musical piece from the one automatically selected by the MPTrain system. For example, the user 102 can easily specify his/her desired workout by either selecting one of the pre-defined workouts or creating a new one (as a simple text file, for example). As shown in FIG. 10, the exemplary user interface 332 displays the name 1004 of the music piece currently being played, the total time 1006 of workout, and the amount of time 1008 that the current music piece has been playing for. The exemplary user interface may also display, for example, the percentage 1010 of battery life left on the sensing device 202, the user's current speed 1012 in steps per minute, the total number of steps in workout 1014, the current heart rate 1016 of the user 102 in term of beats per minute, and the total number of calories burned in the workout 1018.

In addition, the user interface 332 may also display and allow input of personal information concerning the user 102. For example, as shown in FIG. 11, the exemplary user interface 332 displays a number 1100 that identifies the user 102 (a number is preferred rather than a name for privacy reasons), the resting heart rate 1104 of the user 102, the maximum allowed heart rate 1106 of the user 102, and the weight 1108 of the user.

The user interface also allows the user to input his/her weight and it uses the user's personal information to compute total number of calories burned during the workout.

Finally, other embodiments of the invention may provide additional audible feedback to the user such as:
  a. MPTrain produces a warning sound when the user exceeds his/her allowed maximum heart-rate
  b. MPTrain produces two distinct tones to cue the user about his/her need to increase or decrease the current heart-rate
  c. MPTrain uses text-to-speech technology to provide to the user current workout information when requested (by pressing one button on the mobile phone). For example, current heart-rate, total number of calories burned, current pace, total time of workout can all be provided by the user using text-to-speech.

While exemplary embodiments of the invention have been illustrated and described, it will be appreciated that various changes can be made therein without departing from the spirit and scope of the invention.

The embodiments of the invention in which an exclusive property or privilege is claimed are defined as follows:

1. A system that uses data indicating a current physiology and movement speed of a user to select music to assist the user to achieve a desired exercise performance level, comprising:
   a computing device, comprising:
     a data receiver to receive the data indicating the current physiology and movement speed of the user;
     a computing module to compare previously stored data of the user's pace and associated music and the data indicating the current physiology and movement speed of the user against a desired physiology and movement speed provided by the user to select a music piece matching the associated music in at least one of average energy, variance in energy, beat or volume to assist the user achieve the desired physiology and movement speed;
     a media player, in communication with the computing module, to reproduce the music piece to the user; and
     a log database to store the data indicating the current physiology and movement speed of the user and the music piece.

2. The system of claim 1, further comprising a sensing device to collect the data indicating the current physiology and movement speed of the user.

3. The system of claim 2, wherein the sensing device includes one or more sensors to collect the data indicating the current physiology and movement speed of the user.

4. The system of claim 3, wherein the one or more sensors comprise at least one of an accelerometer and an electrocardiogram sensor.

5. The system of claim 2, wherein the sensing device communicates with the computing device through a communication network.

6. The system of claim 5, wherein the communication network is a wireless communication network.

7. The computing system of claim 1, wherein the data indicating current physiology and movement speed of the user includes the current heart rate of the user.

8. The computing system of claim 1, wherein the computing module is to further calculate a current heart rate of the user using the data indicating the current physiology and movement speed of the user.

9. The computing system of claim 1, wherein the computing module is to further store information including one or more of the data indicating the current physiology and movement speed of the user, information on the music piece, and information on the user.

10. The computing system of claim 1, wherein the computing module is to further retrieve the music piece from a music library containing music pieces specific to the user.

11. The computing system of claim 1, wherein the computing module further comprises a user interface.

12. The computing system of claim 1, further comprising a sensing module to collect the data indicating the current physiology and movement speed of the user.

13. The computing system of claim 12, wherein the sensing module comprises a data transmitter to transmit the data indicating the current physiology and movement speed of the user.

14. The computing system of claim 13, wherein the sensing module is to calculate a current heart rate of the user using the data indicating the current physiology and movement speed of the user.

15. A computer-implemented method, comprising:
receiving data indicating a current physiology and movement speed of a user;
receiving previously stored data of the user's pace and associated music from a log database;
receiving a desired physiology and movement speed from the user; and
providing the user a music piece matching the associated music in at least one of average energy, variance in energy, beat or volume based on the data indicating the current physiology and movement speed of the user and the previously stored data of the user's pace and associated music against the desired physiology and movement speed.

16. The method of claim 15, further comprising processing the data indicating the current physiology and movement speed of the user to obtain a current heart rate of the user.

17. The method of claim 15, further comprising storing information including one or more of the data indicating the current physiology and movement speed of the user, information on the music piece, and information on the user.

* * * * *